United States Patent [19]

Fowler et al.

[11] Patent Number: 4,680,295

[45] Date of Patent: Jul. 14, 1987

[54] OCTAHYDROPYRIDO[1,2-C]PYRIMIDINONES AND HEXAHYDROPYRIDO[1,2-C]PYRIMIDINEDIONES

[75] Inventors: Kerry W. Fowler, Chicago; Robert J. Chorvat, Lake Bluff, both of Ill.

[73] Assignee: G. D. Searle & Co., Skokie, Ill.

[21] Appl. No.: 825,723

[22] Filed: Feb. 3, 1986

[51] Int. Cl.$^4$ ............... C07D 471/04; A61K 31/505
[52] U.S. Cl. .................................. 514/258; 544/282; 546/245
[58] Field of Search .................. 544/282; 514/258

[56] References Cited

U.S. PATENT DOCUMENTS 4,560,754 12/1985 Adelstein et al. .............. 544/282
4,567,270 1/1986 Chorvat et al. ................ 546/183

OTHER PUBLICATIONS

L. S. Goodman & A. Gilman, eds., The Pharmacological Basis of Therapeutics, 6th Edition; New York: Macmillan Publishing Co., 1980: pp. 730–731, 750–751, 761–786.

R. J. Chorvat et al., "Synthesis and Structure Activity Relationships of a New Series of Antiarrhythmic Agents . . . ", J. Med. Chem., 28, 1285–1291 (1985).

*Primary Examiner*—Donald G. Daus
*Assistant Examiner*—Barbara Cassatt
*Attorney, Agent, or Firm*—Richard E. L. Henderson; Mary Jo Kanady; Paul D. Matukaitis

[57] ABSTRACT

This invention relates to octahydropyrido[1,2-c]pyrimidinones and hexahydropyrido[1,2-c]pyrimidinediones that are useful as inhibitors of cardiac arrhythmias and are therefore useful in the treatment of irregular heartbeat.

27 Claims, No Drawings

OCTAHYDROPYRIDO[1,2-C]PYRIMIDINONES AND HEXAHYDROPYRIDO[1,2-C]PYRIMIDINEDIONES

BACKGROUND OF THE INVENTION (a) Field of the Invention

This invention relates to octahydropyrido[1,2-c]pyrimidinones and hexahydropyrido[1,2-c]pyrimidinediones that are useful as inhibitors of cardiac arrhythmias and are therefore useful in the treatment of irregular heartbeat.

Arrhythmias are disorders relating to electrical impulse generation in the heart. The disorders include premature contractions (extrasystoles) originating in abnormal or ectopic foci in atria or ventricles; atrial flutter; atrial fibrillation; and ventricular tachycardia and fibrillation. For a discussion on these disorders, see, for example, L. S. Goodman and A. Gilman, eds., *The Pharmacological Basis of Therapeutics*, Sixth Edition; New York: Macmillan Publishing Co., 1980; pp. 761-767.

A number of compounds have been developed to alter cardiovascular function related to heart rate and rhythm. See Goodman and Gilman, pp. 730-731, 750-751, 768-786. The cardiac glycosides, including digitalis, have as their main pharmacodynamic property the ability to increase the force of myocardial contraction. This positive inotropic action is the basis of the salutary effects of these cardiac glycosides in congestive heart failure—increased cardiac output; decreased heart size, venous pressure, and blood volume; and diuresis and relief of edema. Quinidine is useful in the therapy of atrial fibrillation but exhibits several toxic reactions, such as cinchonism. Procainamide acts in essentially the same manner as quinidine, and also exhibits toxic side effects. Lidocaine, a widely used local anesthetic, may be used in the treatment of ventricular arrhythmias, but must be administered by injection. Propranolol is useful in the treatment of supraventricular tachycardias and ventricular arrhythmias, but must be used with great care because it may induce significant hypotension, left ventricular failure, or even cardiovascular collapse. Disopyramide has effects somewhat like procainamide and quinidine, all being so-called Type 1 antiarrhythmics. At therapeutic levels disopyramide shortens the sinus node recovery time, lengthens the effective refractory period of the atrium, and has a minimal effect on the refractory period of the A-V node. However, because of the anticholinergic effects of some of the Type 1 antiarrhythmics, such as disopyramide, they should not be used in patients with glaucoma, myasthenia gravis, or problems of urinary retention.

(b) Prior Art

As previously described, a number of compounds are useful in the treatment of cardiac arrhythmia. U.S. Pat. No. 4,560,754 discloses certain antiarrhythmic 1,3-diazabicyclo[4.4.0]decan-4-ones and 1,3-diazabicyclo[4.4.0]dec-2-en-4-ones, including compounds of the following general structure:

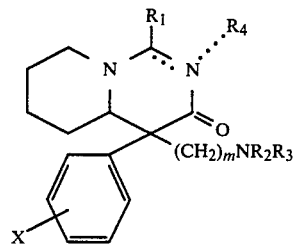

wherein $R_1$ may be hydrogen, lower alkyl, or optionally substituted phenyl; $R_2$ and $R_3$ are lower alkyl; $R_4$ may be hydrogen, but only if the ring nitrogen is not involved in double bonding; and X may be any of several substituents. Thus, in contrast to the present invention, U.S. Pat. No. '754 does not disclose compounds in which $R_1$ is OH, $=$O, $NH_2$, or $=$NH nor compounds in which $R_4$ may be any substituent other than hydrogen.

In addition, U.S. Pat. No. 4,567,270 discloses certain hexahydroindolizinones (or 1-azabicyclo[4.3.0]nonan-9-ones). In contrast to the compounds of the present invention, the hexahydroindolizinones of Ser. No. '210 are characterized by a bicyclic skeleton of fused five- and six-membered rings containing a single ring nitrogen at a bridgehead position and bear substituents around the rings at distinctly different locations.

SUMMARY OF THE INVENTION

The invention relates to compounds of Formula I:

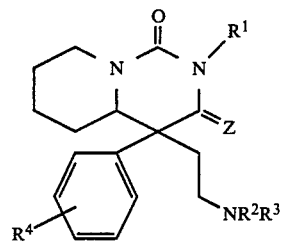

and pharmaceutically acceptable acid addition salts, wherein
$R^1$ is
(a) hydrogen;
(b) $C_1$-$C_6$ alkyl;
(c) $C_2$-$C_6$ hydroxyalkyl; or
(d) $-(CH_2)_n-Y$,
wherein
n is 1 or 2;
Y is:
(a) $C_5$-$C_8$ cycloalkyl; or
(b)

wherein
$R^5$ and $R^6$ independently are:
(a) hydrogen;
(b) $C_1$-$C_6$ alkyl;
(c) $C_1$-$C_6$ alkoxy; or
(d) halogen;
$R^2$ and $R^3$ are independently $C_1$-$C_6$ alkyl;
$R^4$ is:

(a) hydrogen;
(b) $C_1$-$C_6$ alkyl;
(c) $C_1$-$C_6$ alkoxy;
(d) halogen; or
(e) phenyl; and Z is =O or =N-$R^7$,
wherein
$R^7$ is:
(a) hydrogen; or
(b) $C_2$-$C_6$ alkanoyl.

Although the structure shown for Formula I indicates one tautomeric form, it is understood that this representation is for convenience only and that the scope of this invention includes as equivalents all tautomeric forms of the compounds of this invention. Moreover, it is understood that the structure also represents the various isomers and racemates thereof, as illustrated in the Examples.

The term "$C_1$-$C_6$ alkyl" refers to straight or branched chain alkyl groups having from 1 to 6 carbon atoms, also referred to as lower alkyl. Examples of $C_1$-$C_6$ alkyl are methyl, ethyl, propyl, butyl, pentyl, hexyl, and the isomeric forms thereof.

The term "$C_2$-$C_6$ hydroxyalkyl" refers to straight or branched chain alkyl groups having from 2 to 6 carbon atoms and bearing a hydroxy group on a carbon atom other than that to which the ring nitrogen is attached. Examples of $C_2$-$C_6$ hydroxyalkyl are 2-hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, and isomeric forms thereof.

The term "$C_5$-$C_8$ cycloalkyl" encompasses cyclopentyl, cyclohexyl, cycloheptyl, and cyclooctyl.

The term "$C_1$-$C_6$ alkoxy" refers to straight or branched chain alkoxy groups having from 1 to 6 carbon atoms. Examples of $C_1$-$C_6$ alkoxy are methoxy, ethoxy, propoxy, butoxy, pentoxy, hexoxy, and the isomeric forms thereof.

The term "$C_2$-$C_6$ alkanoyl" refers to straight or branched chain alkanoyl groups having from 2 to 6 carbon atoms. Examples of $C_2$-$C_6$ alkanoyl are acetyl, propanoyl, butanoyl, pentanoyl, hexanoyl, and the isomeric forms thereof.

Examples of halogen are fluorine, chlorine, bromine, and iodine.

The term "pharmaceutically acceptable acid addition salt" refers to a salt prepared by contacting a compound of Formula I with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts.

DESCRIPTION OF THE INVENTION

The compounds of this invention may be prepared by the method illustrated in the following Schemes. Unless otherwise specified, the various substituents are defined as for Formula I, above. Scheme A illustrates a method of preparing the hexahydropyrido[1,2-c]pyrimidinediones of this invention.

SCHEME A

Preparation of 2-piperidineacetamides of Formula II is disclosed in U.S. Pat. No. 4,560,754 and further described by R. J. Chorvat et al. in *J. Med. Chem.*, 28, 1285-1291 (1985). Compounds of Formula II are cyclized in a suitable organic solvent containing a suitable base and a suitable carbonylating agent of Formula A-CO-B, wherein A and B are appropriate leaving groups, to yield hexahydropyrido[1,2-c]pyrimidinediones of Formula III. Suitable organic solvents for cyclization are organic liquids in which reactants may be dissolved or suspended but which are otherwise chemically inert. Examples of suitable organic solvents include alkanes and cycloalkanes, ethers and cyclic ethers, aromatic hydrocarbons, N,N-dialkylformamides, and other solvents known in the art. A preferred organic solvent is tetrahydrofuran. Suitable bases for cyclization are chemical compounds that are sufficiently basic to abstract an amide proton from a compound of Formula II so that the cyclization reaction may take place. Examples of suitable bases include alkali metal hydrides, such as sodium hydride and potassium hydride; alkali metal alkoxides, such as sodium methoxide, sodium ethoxide, and potassium t-butoxide; alkali metal alkyls, such as n-butyllithium and t-butyllithium; alkali metal amides, such as sodamide and lithium diisopropylamide. A preferred strong base is sodium hydride. Suitable carbonylating agents of Formula

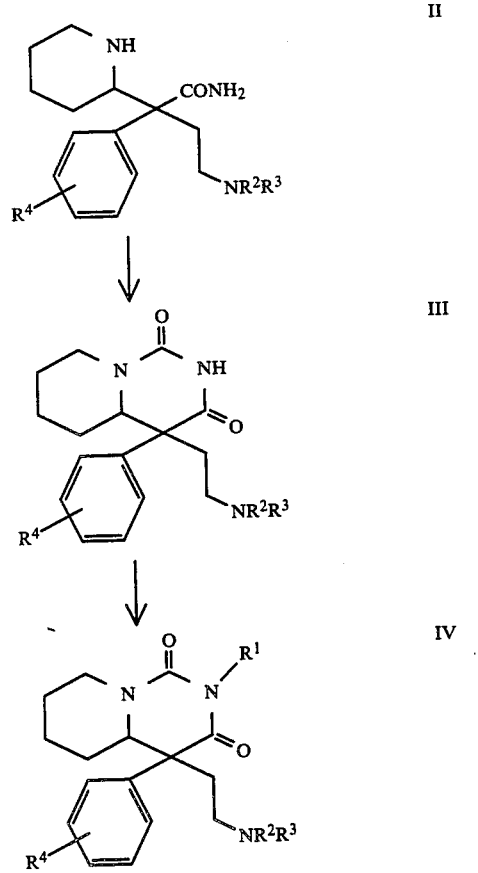

A-CO-B are compounds in which leaving groups A and B are sufficiently labile that the cyclization reaction may take place, but do not render the carbonylating agent so reactive as to dehydrate the amide group to the corresponding nitrile group. That is, suitable carbonylating agents of Formula A-CO-B are compounds in which A is imidazole, alkoxide, and the like, and in which B is imidazole, alkoxide, halogen, alkoxycarbonyl, and the like. Example of suitable carbonylating agents include carbonyldiimidazole, methyl chlorocarbonate, ethyl chlorocarbonate, isopropyl chlorocarbonate, dimethyl carbonate, diethyl carbonate, diethyl dicarbonate, di-t-butyl dicarbonate, and the like. Preferred cyclization conditions employ carbonyldiimidazole in tetrahydrofuran containing sodium hydride.

Hexahydropyrido[1,2-c]pyrimidinediones of Formula III may be alkylated to yield compounds of Formula IV. Alkylations are performed under conditions well known to those in the art. Preferred alkylating conditions employ a $C_1$-$C_6$ alkyl halide in a suitable organic solvent containing a suitable base and a compound of Formula III. Suitable organic solvents for alkylation are organic liquids in which reactants may be dissolved or suspended but which are otherwise chemically inert. Examples of suitable organic solvents include alkanes and cycloalkanes, ethers and cyclic ethers, aromatic hydrocarbons, N,N-dialkylformamides, and other solvents known in the art. Suitable bases for alkylation are chemical compounds that are sufficiently basic to abstract the cyclic amide proton from a compound of Formula III so that alkylation may take place. Examples of suitable bases include alkali metal hydrides, such as sodium hydride and potassium hydride; alkali metal alkoxides, such as sodium methoxide, sodium ethoxide, and potassium t-butoxide; alkali metal alkyls, such as n-butyllithium and t-butyllithium; and alkali metal amides, such as sodamide and lithium diisopropylamide. Preferred alkylation conditions employ $C_1$-$C_6$ alkyl iodides, such as methyl iodide, ethyl iodide, and the like, in dimethylformamide containing sodium hydride.

Scheme B illustrates a method of preparing the octahydropyrido[1,2-c]pyrimidinones of this invention.

SCHEME B

2-Piperidineacetamides of Formula II are allowed to react in a suitable organic solvent containing a suitable carbonylating agent of Formula D-CO-E, wherein D and E are appropriate leaving groups, to yield 2-(1-cyanopropyl)-1-piperidinecarbonyl chlorides of Formula V. Suitable organic solvents for carbonylation are organic liquids in which reactants may be dissolved or suspended but which are otherwise chemically inert. Examples of suitable organic solvents include alkanes and cycloalkanes; ethers

SCHEME B

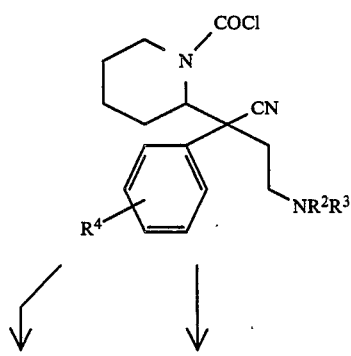

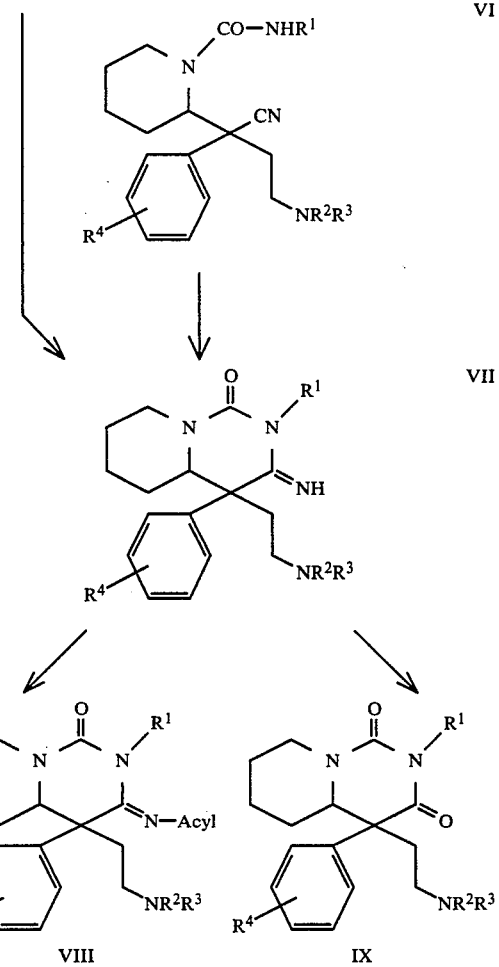

and cyclic ethers; aromatic hydrocarbons; N,N-dialkylformamides; halocarbons, such as chloroform, dichloromethane, ethylene dichloride, and the like; and other solvents known in the art. Suitable carbonylating agents of Formula D-CO-E are compounds that are sufficiently reactive to dehydrate the amide group of Formula II (to form the corresponding nitrile group) while acylating the piperidine nitrogen atom. Examples of appropriate leaving groups D and E include halogens, preferably chlorine. Preferred reaction conditions employ phosgene in chloroform.

Compounds of Formula V may be converted to octahydropyrido[1,2-c]pyrimidinones of Formula VII by reaction with compounds of Formula $R^1NH_2$ using several methods, including two methods illustrated in Scheme B. In one procedure, a 2-(1-cyanopropyl)-1-piperidinecarbonyl chloride of Formula V reacts with a compound of Formula $R^1NH_2$ in a suitable solvent to form an isolable intermediate urea of Formula VI. Suitable organic solvents for the reaction are organic liquids in which reactants may be dissolved or suspended but which are otherwise chemically inert. Examples of suitable organic solvents include ethers and cyclic ethers; N,N-dialkylformamides; lower alkanols, such as methanol, ethanol, propanol, and the like; and other solvents known in the art. Typically, a compound of Formula V is allowed to react in a lower alkanol with an excess of a compound of Formula $R^1NH_2$ or with an approximately equimolar quantity of the compound of Formula $R^1NH_2$ in the presence of a suitable mild base. Suitable bases for the reaction are chemical compounds that are sufficiently basic to prevent the reaction medium from becoming acidic but which do not themselves form significant quantities of byproducts by reaction with compounds of Formula V. Examples of suitable bases include alkali metal carbonates, such as lithium, sodium, or potassium carbonate; and tertiary amines, such as triethylamine, tributylamine, N-methylmorpholine, and the like. For compounds of Formula $R^1NH_2$ wherein $R^1$ is not hydrogen, preferred conditions employ an approximately two-fold molar quantity of the compound of Formula $R^1NH_2$ in ethanol heated at reflux. For ammonia (i.e., Formula $R^1NH_2$ wherein $R^1$ is hydrogen), preferred reaction conditions employ aqueous ammonia dissolved in tetrahydrofuran and stirred at room temperature.

Subsequent treatment of compounds of Formula VI with a suitable base in a suitable organic solvent induces cyclization to form compounds of Formula VII. Suitable bases for cyclization are chemical compounds that are sufficiently basic to abstract an amide proton from a compound of Formula VI so that the cyclization reaction may take place. Examples of suitable bases include alkali metal hydrides, such as sodium hydride and potassium hydride; alkali metal alkoxides, such as sodium methoxide, sodium ethoxide, and potassium t-butoxide; alkali metal alkyls, such as n-butyllithium and t-butyllithium; and alkali metal amides, such as sodamide and lithium diisopropylamide. A preferred base is sodium hydride. Suitable organic solvents for cyclization are organic liquids in which reactants may be dissolved or suspended but which are otherwise chemically inert. Examples of suitable organic solvents include alkanes and cycloalkanes, ethers and cyclic ethers, aromatic hydrocarbons, N,N-dialkylformamides, and other solvents known in the art. A preferred organic solvent is tetrahydrofuran.

Another procedure illustrated in Scheme B for converting compounds of Formula V to octahydropyrido[1,2-c]pyrimidinones of Formula VII also employs compounds of Formula $R^1NH_2$. In this second procedure, however, compounds of Formula VII are obtained without isolating an intermediate urea. Typically, a compound of Formula V is heated at reflux in water or a lower alkanol (such as methanol, ethanol, propanol, and the like) with an excess of a compound of Formula $R^1NH_2$, with or without addition of a suitable mild base. Suitable mild bases for cyclization are chemical compounds that are sufficiently basic to prevent the reaction medium from becoming acidic but which do not themselves form significant quantities of byproducts by reaction with compounds of Formula V. Examples of suitable bases include alkali metal carbonates, such as lithium, sodium, or potassium carbonate; and tertiary amines, such as triethylamine, tributylamine, N-methylmorpholine, and the like. For compounds of Formula $R^1NH_2$ wherein $R^1$ is not hydrogen, preferred conditions employ an excess of the compound of Formula $R^1NH_2$ heated at reflux in ethanol. For ammonia (i.e., Formula $R^1NH_2$ wherein $R^1$ is hydrogen), preferred reaction conditions employ concentrated aqueous ammonia heated at about 80° C. until the corresponding compound of Formula VII forms.

Compounds of Formula VII may be acylated by any number of methods known to those skilled in the art to yield N-acyl compounds of Formula VIII. Preferred acylating conditions employ an alkanoic anhydride (such as acetic anhydride, propanoic anhydride, and the like) in pyridine.

Octahydropyrido[1,2-c]pyrimidinones of Formula VII also provide an alternative preparation of certain hexahydropyrido[1,2-c]pyrimidinediones of this invention. Deamination of compounds of Formula VII employing methods known to those skilled in the art, preferably using nitrous acid prepared in situ, affords hexahydropyrido[1,2-c]pyrimidinediones of Formula IX. Preferred deamination conditions include treating an octahydropyrido[1,2-c]pyrimidinones of Formula VII with an alkali metal nitrite, preferably sodium nitrite, in a dilute aqueous acid, preferably aqueous acetic acid, to yield a compound of Formula IX.

The preferred embodiments of this invention include compounds of the following general structure

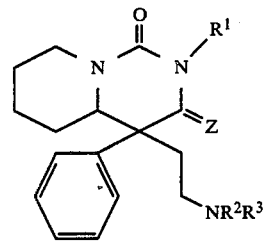

X and pharmaceutically acceptable acid addition salts, wherein $R^1$ is:
 (a) hydrogen;
 (b) methyl;
 (c) hydroxyethyl; or
 (d) $-(CH_2)_n-Y$,
wherein
 n is 1 or 2:
 Y is:
  (a) $C_5-C_8$ cycloalkyl; or
  (b)

(a) $C_5-C_8$ cycloalkyl; or

wherein
 $R^5$ and $R^6$ independently are:
  (a) hydrogen; or
  (b) methoxy;
 $R^2$ and $R^3$ are independently $C_1-C_6$ alkyl; and
 Z is $=O$ or $=N-R^7$,
wherein
 $R^7$ is:
  (a) hydrogen; or
  (b) acetyl.

The most preferred embodiments of this invention include compounds of the following general structure:

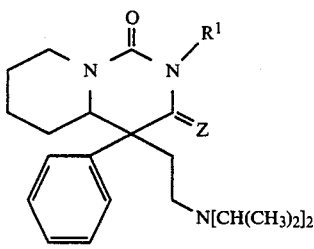

and pharmaceutically acceptable acid addition salts, wherein Z is =O or =N-R$^7$, and wherein R$^7$ is hydrogen or acetyl.

The octahydropyrido[1,2-c]pyrimidinones and hexahydropyrido[1,2-c]pyrimidinediones of this invention exhibited antiarrhythmic activity in dogs in which ventricular arrhythmia was induced by coronary artery ligation. Arrhythmias induced in this manner are considered similar in nature to those resulting from myocardial infarction in humans. Quinidine, procainamide, and disopyramide are active under these conditions and are active in man. The antiarrhythmic activity of the compounds of this invention illustrated in the examples was tested by the following method.

Inhibition of Ventricular Arrhythmia Induced by Coronary Ligation

Ventricular arrhythmia was induced by a two-stage ligation of the anterior descending branch of the left coronary artery in each of two or more dogs. Compounds were administered intravenously using an initial 5 mg/kg body weight dose, with additional doses injected at intervals to a maximum of 20 mg/kg. A compound was rated active if it produced at least a 25% reduction in ectopic beats for a period of at least ten minutes in half or more of the dogs. The average minimum effective dose for each compound was calculated.

Compounds which were lethal or produced 75-100% reduction in the ventricular arrhythmia at the initial 5 mg/kg dose were further tested using 1 mg/kg doses injected as before at five minute intervals. As before, a compound was rated active if it produced at least a 25% reduction in ectopic beats for a period of at least ten minutes in half or more of the dogs. The average minimum effective dose for each compound was calculated.

Table 1 illustrates the antiarrhythmic activity of certain of the preferred compounds of Formula X.

TABLE 1

Inhibition of Ventricular Arrhythmia Induced by Coronary Ligation.

| Compound (Example No.) | Average Minimum Effective Dose (mpk) | Comments |
| --- | --- | --- |
| 4, 6 | 8.75 | |
| 7 | 7.5 | |
| 9 | 1.2 | |
| 10 | 3.0 | |
| 11, 12 | 11.3 | |
| 13 | 15.0 | |
| 14 | 10.0 | |
| 15 | 1.0 | |
| 16 | <3.0 | Approx. activity |
| 17 | 4.2 | |
| 18 | 2.5 | |
| 19 | 12.5 | |
| Disopyramide | 9.2 | Human dose (i.v.) ca. 2 mpk |

By virtue of their antiarrhythmic activity, the compounds of Formula I are useful in treating cardiac arrhythmia in mammals. A physician or veterinarian of ordinary skill can readily determine whether a subject exhibits cardiac arrhythmia. Regardless of the route of administration selected, the compounds of the present invention are formulated into pharmaceutically acceptable dosage forms by conventional methods known to those skilled in the art. The compounds may be formulated using pharmacologically acceptable acid addition salts. Moreover, the compounds or their salts may be used in a suitable hydrated form.

The compounds can be administered in such oral dosage forms as tablets, capsules, pills, powders, granules, elixirs, or syrups. They may also be administered intravascularly, intraperitoneally, subcutaneously, or intramuscularly, using forms known to the pharmaceutical art. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, active drug components may be combined with a suitable carrier such as water, saline, aqueous dextrose, and the like.

By whatever route of administration selected, an effective but non-toxic quantity of the compound is employed in treatment. The dosage regimen for treating arrhythmia with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of about 0.1 mg/kg up to about 20 mg/kg.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

EXAMPLE 1

(±) αR*-[2-[bis(1-methylethyl)amino]ethyl]-α-phenyl-2R*-piperidineacetamide ("Racemate A")

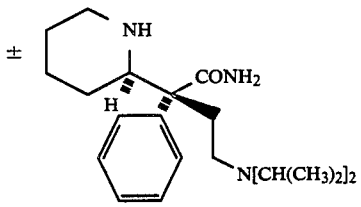

A mixture of 105 g (0.31 mole) of racemic 2-phenyl-2-(2-pyridyl)-4-[N,N-bis(1-methylethyl)amino]butanamide and 27 ml (ca. 0.32 mole) of concentrated aqueous hydrochloric acid in 2.5 liters of ethanol was hydrogenated at 50 psi using platinum oxide as catalyst. The reaction mixture was filtered and the filtrate was concentrated in vacuo. The resultant syrupy residue was dissolved in an ice-water mixture, neutralized with a slight excess of 25% aqueous sodium hydroxide, and extracted with diethyl ether. The ether layer was dried over magnesium sulfate, filtered, and concentrated to dryness. The crude product was crystallized twice from hexane containing a small amount of diethyl ether to yield 26 g of the title compound as a white solid, m.p. 107°–108°. Structure assignment was supported by the nmr spectrum. nmr (CDCl$_3$): δ(ppm) 0.83, 0.92, 7.33

EXAMPLE 2

(±) αR*-[2-[bis(1-methylethyl)amino)ethyl]-α-phenyl-2S*-piperidineacetamide ("Racemate B")

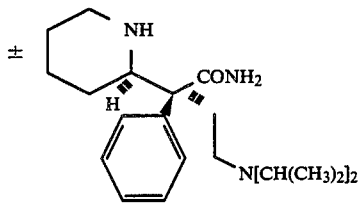

The final filtrate from Example 1 was concentrated under a stream of nitrogen gas to an oil that slowly solidified. Chromatography on silica gel afforded 17 g of the title compound as a white solid, m.p. 81°–82°. Structure assignment was supported by the nmr spectrum. nmr (CDCl$_3$): δ(ppm) 0.96, 1.05, 7.30

EXAMPLE 3

(±)2R*-[3-[bis(1-methylethl)amino)-1R*-cyano-1-phenylpropyl]-1-piperidinecarbonyl chloride

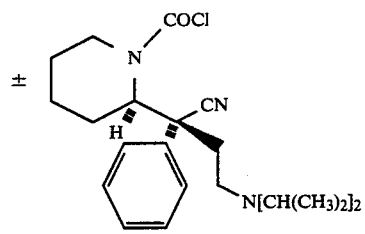

To a cold (ca. 0°) solution of 22.5 g (65.2 mmole) of (±) αR*-[2-[bis(1-methylethyl)amino]ethyl]-α-phenyl-2R*-piperidineacetamide ("Racemate A") in 200 ml of chloroform stirred under argon was added dropwise 117 ml of 1.26 M phosgene in toluene. One hour after addition was completed, the mixture was poured into saturated aqueous sodium bicarbonate. The chloroform layer was separated, washed successively with water and saturated brine, dried over magnesium sulfate, filtered, and concentrated in vacuo. Recrystallization of the residue from heptane afforded 22.5 g (in two crops) of the title compound as a white powder, m.p. 128.5°–129°. Structure assignment was supported by spectral data and by the elemental analysis.

Infrared (CHCl$_3$): 3980, 2230, 1725 cm$^{-1}$

Mass spectrometry: m/z 389 (M$^+$), 374 (M-15), 146, 114 nmr (CDCl$_3$): δ(ppm) 0.94 (d, 12H, isopropyl CH$_3$'s); 1.4–2.5 (m); 2.95 (m, 2H, isopropyl CH's); 4.70 (m); 7.25–7.6 (m, 5H, phenyl CH's)

Analysis. Calcd. for C$_{22}$H$_{32}$N$_3$OCl: C, 67.76; H, 8.27; N, 10.78; Cl, 9.09. Found: C, 67.75; H, 8.30; N, 10.77; Cl, 9.06.

EXAMPLE 4

(±)trans-3-amino-4-[2-[bis(1-methylethyl)amino)ethyl]-4,4a,5,6,7,8-hexahydro-4-phenyl-1H-pyrido[1,2-c]pyrimidin-1-one, Method A

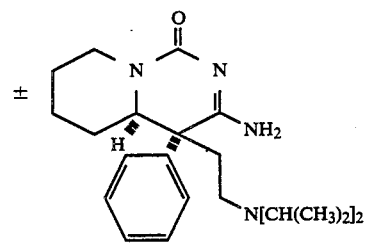

A suspension of 3.0 g (7.7 mmole) of (±) 2R*-[3-[bis(1-methylethyl)amino)-1R*-cyano-1-phenylpropyl]-1-piperidinecarbonyl chloride in 100 ml of concentrated ammonium hydroxide was heated overnight at 80°. The mixture was extracted with chloroform, and the organic layer was washed successively with water and brine, dried over magnesium sulfate, filtered, and concentrated in vacuo to a gummy residue. Flash chromatography on silica gel (using 85:14:1 chloroform-ethanol-ammonium hydroxide as eluent) yielded 1.7 g of the title compound as a hygroscopic solid. Structure assignment was supported by spectral data.

Infrared (CHCl₃) 3440, 3000, 2980, 2860, 1675, 1650, 1560 cm⁻¹.

Mass spectrometry: m/z 327 (M-isopropyl), 270, 242, 187, 128, 114, 84 nmr (CDCl₃): δ(ppm) 0.87 (d, 12H, isopropyl CH₃'s); 1.3-3.6 (complex m's); 4.33 (br d); 7.33 (s, 5H, phenyl CH's)

EXAMPLE 5

(±) 2R*-[3-[bis(1-methylethyl)amino]1R*-cyano-1-phenyl-propyl]-1-piperidinecarboxamide, monohydrate

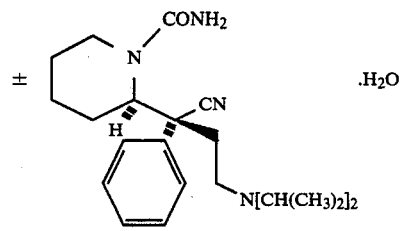

A solution of 1.0 g (2.6 mmole) of (±) 2R*-[3-[bis(1-methylethyl)aminol-1R*-cyano-1-phenylpropyl]-1-piperidinecarbonyl chloride and 2 ml of concentrated aqueous ammonium hydroxide in 6 ml of tetrahydrofuran was stirred at room temperature. After 18 hours, the mixture was concentrated in vacuo. The residue was dissolved in dichloromethane, washed successively with water and brine, dried over magnesium sulfate, filtered, and concentrated in vacuo to yield 0.94 g of the title compound as a white foam, which was homogeneous by thin-layer chromatography (85:14:1 chloroform-ethanol-ammonium hydroxide on silica gel). Structure assignment was supported by spectral data and by elemental analysis.

Infrared (CHCl₃): 3500, 3400, 2995, 2980, 2220, 1650, 1580 cm⁻¹.

Mass spectrometry: m/z 355 (M-15), 244, 229, 187, 127, 114, 84 nmr (CDCl₃) δ(ppm) 0.94 (d, 12H, isopropyl CH₃'s); 1.3-3.4 (m); 4.23 (br s, 2H, NH₂; exchanged with D₂O); 4.63 (br t); 7.30-7.67 (m, 5H, phenyl CH's)

Analysis. Calcd. for C₂₂H₃₄N₄O.H₂O: C, 68.00 H, 9.34; N, 14.42. Found: C, 68.50; H, 8.98; N, 14.26.

EXAMPLE 6

(±)trans-3-amino-4-[2-[bis(1-methylethyl) amino]ethyl)-4,4a,5,6,7,8-hexahydro-4-phenyl-1H-pyrido[1,2-c)pyrimidin-1-one, Method B The title compound was prepared by the method of Example 9 (below) using (±) 2R*-[3-[bis(1-methylethyl)amino)-1R*- cyano-1-phenylpropyl]-1-piperidinecarboxamide instead of (±) 2R*-[3-[bis(1-methylethyl)amino]-1R*-cyano-1-phenylpropyl)-N-[2-(3,4-dimethoxyphenyl)ethyl]-1-piperidinecarboxamide.

EXAMPLE 7

(±)trans-N-[4-[2-[bis(1-methylethyl)amino]ethyl]-4,4a,5,6,7,8-hexahydro-1-oxo-4-phenyl-1H-pyrido[1,2-c]pyrimidin-3-yl]acetamide

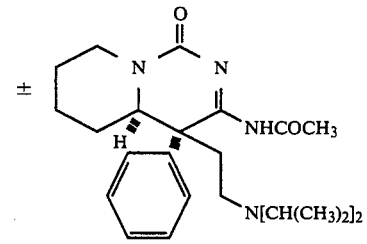

A mixture of 3.5 g (9.4 mmole) of (±)trans-3-amino-4-[2-[bis(1-methylethyl)aminoethyl]-4,4a,5,6,7,8-hexahydro-4-phenyl-1H-pyrido[1,2-c]pyrimidin-1-one and 1.0 g (9.8 mmole) of acetic anhydride in 25 ml of pyridine was stirred for three days at room temperature. After volatiles were removed under a stream of nitrogen, the residue was dissolved in chloroform and washed successively with aqueous sodium bicarbonate, water, and brine. The chloroform layer was dried over magnesium sulfate, filtered, and concentrated in vacuo to a white solid. Recrystallization from ethyl acetate afforded 2.8 g (in two crops) of the title compound as a white powder, m.p. 176-178° . Structure assignment was supported by spectral data and by the elemental analysis.

Infrared (CHCl₃) 3380, 3230, 2970, 1690, 1590, 1470, 1365 cm⁻¹.

Mass spectrometry: m/z 410 (M-2), 397 (M-15), 327 (M-43), 312 (M-100), 285 (M-127), 284, 270, 149, 128, 127, 84 nmr (CDCl₃): δ(ppm) 0.80, 0.85 (pair d, J=10 Hz, 12 H, isopropyl CH₃'s); 1.25-2.2 (m); 2.30 (s, 3H, acetyl CH₃); 2.85 (m, 2H, isopropyl CH's); 3.75 (d, J=10 Hz, 1H); 4.25 (d, J=12.5 Hz, 1H); 7.28 (s, 5H, phenyl CH's)

Analysis. Calcd. for C₂₄H₃₆N₄O₂: C, 69.87; H, 8.80; N, 13.58. Found: C, 69.67; H, 8.70; N, 13.46.

EXAMPLE 8

(±) 2R*-[3-[bis(1-methylethyl)amino]-1R*cyano-1-phenyl-propyl]-N-[2-(3,4-dimethoxyphenyl)ethyl]-1-piperidinecarboxamide

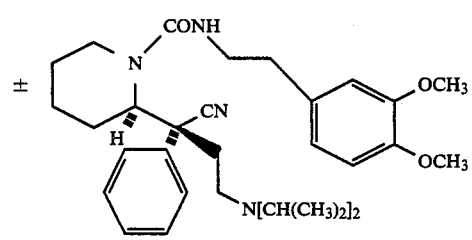

A solution of 1.5 g (4.0 mmole) of (±) 2R*-[3-[bis(1-methylethyl)amino]-1R*-cyano-1-phenylpropyl]-1-piperidine-carbonyl chloride and 1.5 g (8.1 mmole) of 3,4-dimethoxyphenethylamine in 25 ml of ethanol was heated at reflux overnight and then concentrated in vacuo to a gum. Flash chromatography on silica gel (using 92.5:7:0.5 chloroform-ethanol-ammonium hydroxide as eluent) afforded 1.6 g of the title compound as the free base. Structure assignment was supported by spectral data.

Infrared (CHCl₃): 3450, 3420, 2960, 2240 (CN), 1640, 1510 cm$^{-1}$

Mass spectrometry: m/z 534 (M+), 519, 491, 291, 229, 164, 151 nmr (CDCl₃): δ(ppm) 0.94 (d, 12H, isopropyl CH₃'s); 1.2–3.4 (m); 3.83 (s, 6H, OCH₃'s); 4.70 (m); 6.47–6.83 (m, 3H, dimethoxyphenyl CH's); 7.3–7.6 (m, 5H, phenyl CH's)

The hydrochloride salt of the title compound was also formed by bubbling hydrogen chloride gas into a solution of the free base of the title compound in diethyl ether. Filtration and drying in vacuo yielded 1.5 g of the hydrochloride salt.

Analysis. Calcd. for $C_{32}H_{46}N_4O_3 \cdot HCl$ C, 67.28; H, 8.30; N, 9.81; Cl, 6.21. Found: C, 67.05; H, 8.24; N, 9.63; Cl, 6.48.

EXAMPLE 9

(±)trans-4-[2-[bis(1-methylethyl)amino)ethyl]-2-[2-(3,4-dimethoxyphenyl)ethyl]octahydro-3-imino-4-phenyl-1H-pyrido [1,2-c]pyrimidin-1-one, dihydrochloride monohydrate

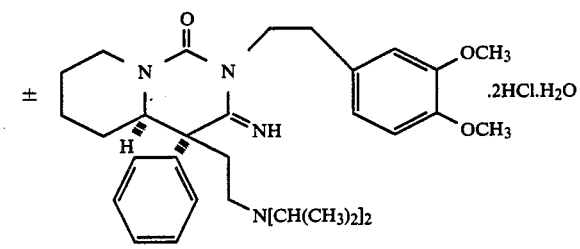

To suspension of 4.2 mmole of oil-free sodium hydride in 2 ml of tetrahydrofuran was added a solution of 1.4 g (2.6 mmole) of (±) 2R*-[3-[bis(1-methylethyl)amino]-1R*-cyano-1-phenylpropyl)-N-[2-(3,4-dimethoxyphenyl)ethyl]-1-piperidinecarboxamide in 10 ml of tetrahydrofuran. The mixture was heated at reflux for one hour and then quenched carefully with water. The mixture was extracted with chloroform, and the organic layer was washed successively with water and brine, dried over magnesium sulfate, filtered, and concentrated in vacuo. The residue was dissolved in diethyl ether and acidified with excess hydrochloride in dioxane. The resultant solid was filtered to give 1.2 g of the title compound as the dihydrochloride salt. Structure assignment was supported by spectral data and by the elemental analysis.

Infrared (KBr): 3400, 2940, 2680, 1715 cm$^{-1}$

Mass spectrometry (free base): m/z 534 (M+), 491, 434, 407, 406, 378, 327, 312, 270, 256, 243, 164, 128, 114 nmr (CDCl₃) δ(ppm) 0.85 (d, J=6 Hz, 3H, isopropyl CH₃); 0.90 (d, 3H, isopropyl CH₃); 1.2–3.2 (m); 3.80, 3.83 (pair s, 6H, OCH₃'s); 3.4–4.4 (m); 6.77 (s, 3H, dimethoxyphenyl CH's); 7.23 (s, 5H, phenyl CH's)

Analysis. Calcd. for $C_{32}H_{46}N_4O_3 \cdot 2HCl \cdot H_2O$: C, 61.42; H, 8.06; N, 8.96; Cl, 11.33. Found: C, 61.21; H, 7.93; N, 8.71; Cl, 11.98.

EXAMPLE 10

(±)cis-4-[2-[bis(1-methylethyl)amino]ethyl]-2-[2-(3,4-dimethoxyphenyl)ethyl]octahydro-3-imino-4-phenyl-1H-pyrido[1,2-c]pyrimidin-1-one, dihydrochloride monohydrate

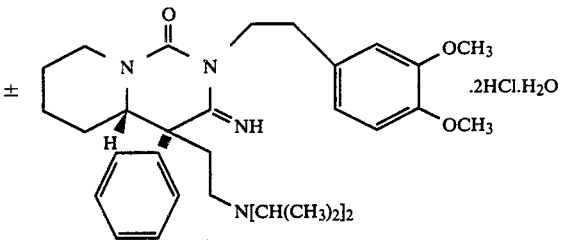

The title compound was prepared by the methods described in Examples 3, 8, and 9 using (±) αR*-[2-[bis(1-methylethyl)amino]ethyl]-α-phenyl-2S*-piperidineacetamide ("Racemate B"; see Example 2) instead of (±) 2R*-[2-[bis(1-methylethyl)amino]ethyl]-α-phenyl-2-R*piperidineacetamide ("Racemate A"; see Example 1). Structure assignment was supported by spectral data and by the elemental analysis.

Infrared (KBr): 3420, 2950, 2680, 1720 cm$^{-1}$

Mass spectrometry (free base): m/z 491 (M-isopropyl), 434, 406, 164 nmr (D₂O): δ(ppm) 1.31 (d, J=7 Hz, 12 H, isopropyl CH₃'s); 3.80, 3.86 (pair s, 6H, OCH₃'s); 6.90–7.65 (m, 8H, aromatic CH's)

Analysis. Calcd. for $C_{32}H_{46}N_4O_3 \cdot 2HCl \cdot H_2O$: C, 61.43; H, 8.06; N, 8.96; Cl, 11.33. Found: C, 61.33; H, 8.00; N, 8.63; Cl, 12.03.

EXAMPLE 11

(±)trans-4-[2-[bis(1-methylethyl)amino]ethyl]hexahydro-4-phenyl-1H-pyrido[1,2-c]pyrimidine-1,3(2H)-dione, Method A

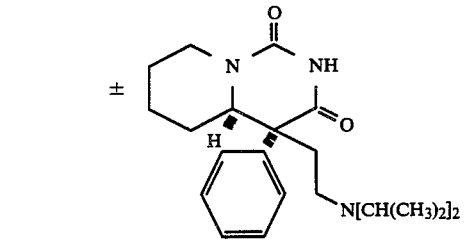

To a suspension of 88 mmole of oil-free sodium hydride in 40 ml of tetrahydrofuran was added a solution of 10.0 g (28.9 mmole) of (±) 2R*-[3-[bis(1-methylethyl)amino]-1R*-cyano-1-phenylpropyl]-1-piperidine (see Example 1) in 50 ml of tetrahydrofuran. Carbonyl diimidazole (7.2 g, 44 mmole) was added cautiously with cooling. The mixture was heated at reflux for two hours and then poured onto crushed ice. The mixture was extracted with three portions of diethyl ether, and the organic layer was washed successively with water and brine, dried over magnesium sulfate, filtered, and concentrated in vacuo to a white solid. Recrystallization from ethyl acetate-hexane afforded 7.6 g of the title compound as a white powder, m.p. 182.5–185°. Structure assignment was supported by spectral data and by the elemental analysis.

Infrared (CHCl₃) 3380, 2950, 1690 cm$^{-1}$

Mass spectrometry (chemical ionization): m/z 371.9 (MH+)

nmr (CDCl3) δ(ppm) 0.82, 0.88 (pair d, 12H, isopropyl CH3's); 1.2-2.9 (m); 2.90 (m, 2H, isopropyl CH's); 3.77 (m); 4.33 (br d); 7.30 (s, 5H, phenyl CH's)

Analysis. Calcd. for C22H33N3O2:C., 71.12; H, 8.95; N, 11.31. Found: C, 70.79; H, 9.00; N, 11.20.

EXAMPLE 12

(±)trans-4-[2-[bis(1-methylethyl)amino]ethyl]hexahydro-4-phenyl-1H-pyrido[1,2-c]pyrimidine-1,3(2H)-dione, Method B To a solution of 2.9 g (7.8 mmole) of (±)trans-3-amino-4-[2-[bis(1-methylethyl)amino]ethyl]-4,4a,5,6,7,8-hexahydro-4 -phenyl-1H-pyrido[1,2-c]pyrimidin-1-one in aqueous acetic acid was added in portions 1.0 g (14.5 mmoles) of sodium nitrite in water. After being stirred overnight at room temperature, the mixture was concentrated in vacuo. The residue was partitioned between ethyl acetate and aqueous potassium hydroxide, and the organic layer was concentrated in vacuo. Recrystallization from ethyl acetate-hexane afforded 1.2 g of the title compound, which was identical to that of Example 11.

EXAMPLE 13

(±)trans-4-[2-[bis(1-methylethyl)amino]ethyl]hexahydro-2-methyl-4-phenyl-1H-pyrido [1,2-c]pyrimidine-1,3(2H)-dione

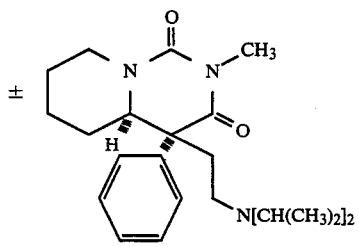

To a suspension of 6.0 mmole of oil-free sodium hydride in 15 ml of dry dimethylformamide was added a solution of 1.5 g (4.0 mmole) of (±)trans-4-[2-[bis(1-methylethyl)amino]ethyl]hexahydro-4-phenyl-1H-pyrido[1,2-c]pyrimidine-1,3(2H)-dione in 7 ml of dimethylformamide. After evolution of hydrogen had subsided, 0.5 ml (8 mmole) of methyl iodide was added. The mixture was stirred for 30 minutes and poured into water. The mixture was extracted with diethyl ether, and the organic layer was washed with water, dried over magnesium sulfate, filtered, and concentrated in vacuo. Recrystallization from heptane afforded 1.1 g of the title compound, m.P. 105°-107°. Structure assignment was supported by spectral data and by the elemental analysis.

Infrared (KBr): 2950, 2850, 1700, 1650, 1465, 1440 cm$^{-1}$

Mass spectrometry: m/z 385 (M+), 370 (M-15), 342 (M-43), 285 (M-100), 257 (M-128), 202, 114 nmr (CDCl3): δ(ppm) 0.82, 0.88 (pair d, 12H, isopropyl CH3's); 1.3-2.3 (m); 2.83 (m, 2H, isopropyl CH's); 3.17 (s, 3H, NCH3); 3.70 (br d, J=11 Hz); 4.30 (br d, J=14 Hz); 7.17 (s, 5H, phenyl CH's)

Analysis. Calcd. for C23H35N3O2: C, 71.65; H, 9.15; N, 10.90. Found: C, 71.37; H, 9.51; N, 10.55.

EXAMPLE 14

(±)trans-4-[2-[bis(1-methylethyl)amino]ethyl]octahydro-3-imino-2-methyl-4-phenyl-1H-pyrido[1,2-c]pyrimidin-1-one, dihydrochloride monohydrate

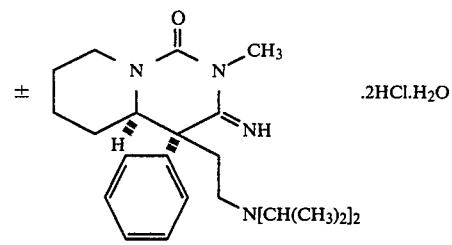

The free base of the title compound was prepared by the method of Example 4 using 40% aqueous methylamine instead of ammonium hydroxide. The free base was converted to the dihydrochloride salt as described in Example 8. Structure assignment was supported by spectral data and by the elemental analysis.

Infrared (free base in CHCl3) 3320, 3300, 2960, 1670, 1615, 1470, 1450 cm$^{-1}$ Mass spectrometry: m/z 341 (M-isopropyl), 284, 257, 256, 228, 201, 114 nmr (free base in CDCl3) δ(ppm) 0.90 (br d, 12H, isopropyl CH3's); 1.2-3.6 (m); 3.30 (s, 3H, NCH3); 4.33 (br d); 7.23 (s, 5H, phenyl CH's)

Analysis. Calcd. for C23H36N4O.2HCl.H2O: C, 58.09; H, 8.48; N, 11.28; Cl, 14.91. Found: C, 58.13;, H, 8.35; N, 11.54; Cl, 14.66.

EXAMPLE 15

(±)trans-4-[2-[bis(1-methylethyl)amino]ethyl]-2-hexyloctahydro-3-imino-4-phenyl-1H-pyrido[1,2-c]pyrimidin-1-one

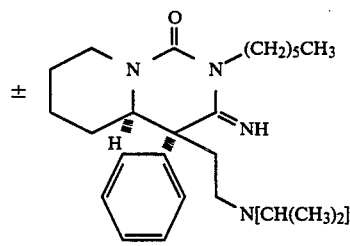

The title compound, m.p. 132.5°-134.5°, was prepared by the methods of Examples 8 and 9 using hexylamine instead of 3,4-dimethoxyphenethylamine and was isolated as the free base rather than as a hydrochloride salt. The compound was recrystallized from hexane. Structure assignment was supported by spectral data and by the elemental analysis.

Infrared (CHCl3): 3350, 3320, 1670, 1615 cm$^{-1}$ nmr (CDCl3): δ(ppm) 0.83, 0.88 (pair d, 12H, isopropyl CH3's); 1.1-2.25 (m); 2.90 (m, 2H, isopropyl CH's); 3.60 (br d); 3.89 (br t); 4.30 (br d, J=13 Hz); 7.25 (s, 5H, phenyl CH's)

Analysis. Calcd. for C28H46N4O: C, 73.96; H, 10.20; N, 12.32. Found: C, 73.70; H, 10.30; N, 12.36.

EXAMPLE 16

(±)trans-4-[2-[bis(1-methylethyl)amino]ethyl]octahydro-3-imino-4-phenyl-2-(2-phenylethyl)-1H-pyrido[1,2-c]pyrimidin-1-one, dihydrochloride 1.7 hydrate

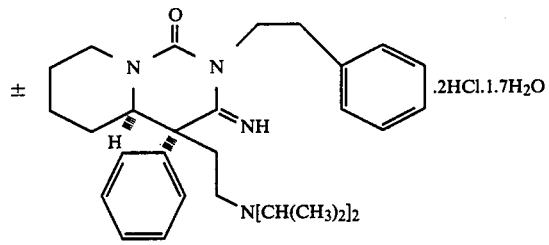

.2HCl.1.7H$_2$O

The title compound was prepared by the methods of Examples 8 and 9 using phenethylamine instead of 3,4-dimethoxyphenethylamine. Structure assignment was supported by spectral data and by the elemental analysis.

Infrared (CHCl$_3$): 1720 cm$^{-1}$ nmr (D$_2$O): δ(ppm) 1.00 (pseudo t, 6H, isopropyl CH$_3$'s); 1.33 (d, 6H, isopropyl CH$_3$'s); 6.90–7.65 (m, 5H, phenyl CH's)

Analysis. Calcd. for C$_{30}$H$_{42}$N$_4$O.2HCl.1.7H$_2$O: C, 62.31; H, 7.97; N, 9.69; Cl, 12.26. Found: C, 62.27; H, 8.18; N, 9.61; Cl, 12.39.

EXAMPLE 17

(±)trans-4-[2-[bis(1-methylethyl)amino]ethyl]-2-(2-cyclohexylethyl)octahydro-3-imino-4-phenyl-1H-pyrido[1,2-c]pyrimidin-1-one

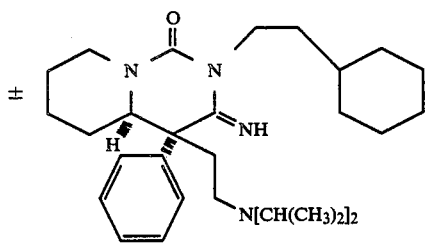

The title compound, m.p. 134.5°–136°, was prepared by the methods of Examples 8 and 9 using 2-(cyclohexyl)ethylamine instead of 3,4-dimethoxyphenethylamine and was recrystallized from heptane-dichloromethane. Structure assignment was supported by spectral data and by the elemental analysis.

Infrared (CHCl$_3$) 3340, 3320, 2970, 2880, 1660, 1610, 1465, 1445 cm$^{-1}$

Mass spectrometry: m/z 481 (M+H), 437, 380, 353, 324 nmr (D$_2$O): δ(ppm) 0.86 (d, J=6 Hz, 6H, isopropyl CH$_3$'s); 0.91 (d, J=6 Hz, 6H, isopropyl CH$_3$'s); 1.0–2.3 (m); 2.93 (m, 2H, isopropyl CH's); 3.63 (br d); 3.95 (br t); 4.40 (br d, J=13 Hz); 7.28 (s, 5H, phenyl CH's)

Analysis. Calcd. for C$_{30}$H$_{48}$N$_4$O: C, 74.95; H, 10.06; N, 11.66. Found: C, 75.06; H, 10.31; N, 11.71.

EXAMPLE 18

(±)trans-4-[2-[bis(1-methylethyl)amino]ethyl]-2-(2-cyclohexylmethyl)octahydro-3-imino-4-phenyl-1H-pyrido[1,2-c]pyrimidin-1-one, dihydrochloride 1.25 hydrate

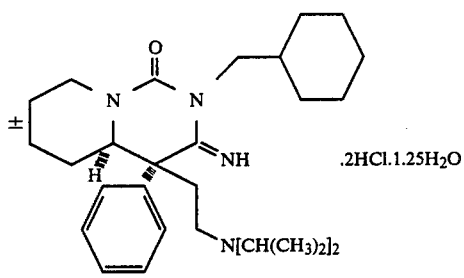

.2HCl.1.25H$_2$O

The title compound was prepared by the methods of Examples 8 and 9 using cyclohexylmethylamine instead of 3,4-dimethoxyphenethylamine. Structure assignment was supported by spectral data and by the elemental analysis.

Infrared (KBr): 2930, 2850, 1720 cm$^{-1}$

Mass spectrometry: m/z 423 (M-isopropyl), 366, 339, 338, 283, 270, 186, 114, 84 nmr (D$_2$O): δ(ppm) 7.50 (s, 5H, phenyl CH's)

Analysis. Calcd. for C$_{29}$H$_{46}$N$_4$O.2HCl.1.25H$_2$O: C, 61.96; H, 9.05; N, 9.97; Cl, 12.61. Found: C, 61.93; H, 8.76; N, 9.79; Cl, 12.99.

EXAMPLE 19

(±)trans-4-[2-[bis(1-methylethyl)amino]ethyl]octahydro-2-(2-hydroxyethyl)-3-imino-4-phenyl-1H-pyrido[1,2-c]pyrimidin-1-one

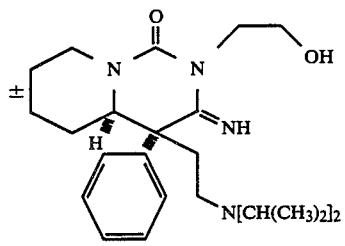

The title compound, m.p. 124°–125°, was prepared by the methods of Examples 8 and 9 using ethanolamine instead of 3,4-dimethoxyphenethylamine and was recrystallized from ethyl acetate-hexane. Structure assignment was supported by spectral data and by the elemental analysis.

Infrared (CHCl$_3$) 3360, 3340, 3200, 2970, 1670, 1615, 1465, 1445 cm$^{-1}$

Mass spectrometry: m/z 371 (M-isopropyl) 314, 287, 286, 268, 114 nmr (CDCl$_3$): δ(ppm) 0.86 (d, J=12 Hz, 6H, isopropyl CH$_3$'s); 1.55 (br m); 1.95 (m); 2.91 (m, 2H, isopropyl CH's); 3.5–4.4 (m); 7.25 (m, 5H, phenyl CH's); 8.45 (s, 1H, OH; exchanged with D$_2$O)

Analysis. Calcd. for C$_{24}$H$_{38}$N$_4$O$_2$: C, 69.53; H, 9.24; N, 13.02. Found: C, 69.11; H, 9.17; N, 13.23.

What is claimed is:

1. A compound of the formula:

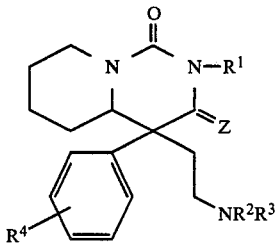

and pharmaceutically acceptable acid addition salts, wherein $R^1$ is:
(a) hydrogen;
(b) $C_1$-$C_6$ alkyl;
(c) $C_2$-$C_6$ hydroxyalkyl; or
(d) —$(CH_2)_n$—Y,
wherein
n is 1 or 2;
Y is:
(a) $C_5$-$C_8$ cycloalkyl; or
(b)

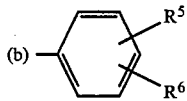

wherein
$R_5$ and $R_6$ independently are:
(a) hydrogen;
(b) $C_1$-$C_6$ alkyl;
(c) $C_1$-$C_6$ alkoxy; or
(d) halogen;
$R^2$ and $R^3$ are independently $C_1$-$C_6$ alkyl;
$R^4$ is:
(a) hydrogen;
(b) $C_1$-$C_6$ alkyl;
(c) $C_1$-$C_6$ alkoxy;
(d) halogen; or
(e) phenyl; and
Z is =O or =N-$R^7$,
wherein
$R^7$ is:
(a) hydrogen; or
(b) $C_2$-$C_6$ alkanoyl.

2. A compound according to claim 1 having the formula:

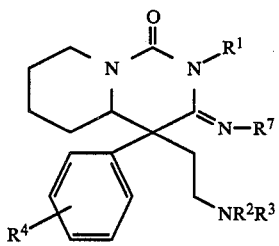

and pharmaceutically acceptable acid addition salts, wherein
$R^1$ is:
(a) hydrogen;
(b) $C_1$-$C_6$ alkyl;
(c) $C_2$-$C_6$ hydroxyalkyl; or
(d) —$(CH_2)_n$—Y,
wherein
n is 1 or 2;
Y is:
(a) $C_5$-$C_8$ cycloalkyl; or
(b)

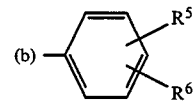

wherein
$R^5$ and $R^6$ independently are:
(a) hydrogen;
(b) $C_1$-$C_6$ alkyl;
(c) $C_1$-$C_6$ alkoxy; or
(d) halogen;
$R^2$ and $R^3$ are independently $C_1$-$C_6$ alkyl;
$R^4$ is:
(a) hydrogen;
(b) $C_1$-$C_6$ alkyl;
(c) $C_1$-$C_6$ alkoxy;
(d) halogen; or
(e) phenyl; and
$R^7$ is:
(a) hydrogen; or
(b) $C_2$-$C_6$ alkanoyl.

3. A compound according to claim 2 wherein $R^4$ is hydrogen.

4. A compound according to claim 3 having the formula:

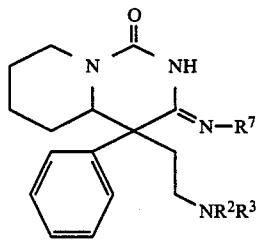

and pharmaceutically acceptable acid addition salts, wherein
$R^2$ and $R^3$ are independently $C_1$-$C_6$ alkyl; and
$R^7$ is:
(a) hydrogen; or
(b) $C_2C_6$ alkanoyl.

5. A compound according to claim 4, which is (±)trans-3-amino-4-[2-[bis(1-methylethyl)amino]ethyl]-4,4a,5,6,7,8-hexahydro-4-phenyl-1H-pyrido [1,2-c]pyrimidin-1-one.

6. A compound according to claim 4, which is (±)trans-N-[4-[2-[bis(1-methylethyl)amino]ethyl]-4,4a,5,6,7,8-hexahydro-1-oxo-4-phenyl-1H-pyrido[1,2-c]pyrimidin-3-yl]acetamide.

7. A compound according to claim 3 having the formula:

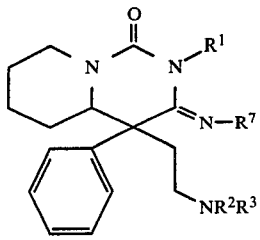

and pharmaceutically acceptable acid addition salts, wherein $R^1$ is $C_1$–$C_6$ alkyl; and
$R^2$ and $R^3$ are independently $C_1$–$C_6$ alkyl; and
$R^7$ is:
(a) hydrogen; or
(b) $C_2$–$C_6$ alkanoyl.

8. A compound according to claim 7, which is (±)trans-4-[2-[bis(1-methylethyl)amino]ethyl]octahydro-3-imino-2-methyl-4-phenyl-1H-pyrido[1,2-c]pyrimidin-1-one.

9. A compound according to claim 7, which is (±)trans-4-[2-[bis(1-methylethyl)amino]ethyl]-2-hexyloctahydro-3-imino-4-phenyl-1H-pyrido [1,2-c]pyrimidin-1-one.

10. A compound according to claim 3 having the formula:

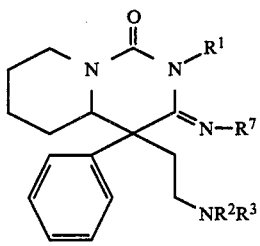

and pharmaceutically acceptable acid addition salts, wherein $R^1$ is $C_2$–$C_6$ hydroxyalkyl;
$R^2$ and $R^3$ are independently $C_1$–$C_6$ alkyl; and $R^7$ is:
(a) hydrogen; or
(b) $C_2$–$C_6$ alkanoyl.

11. A compound according to claim 10, which is (±)trans-4-[2-[bis(1-methylethyl)amino]ethyl]octahydro-2-(2-hydroxyethyl)-3-imino-4-phenyl-1H-pyrido[1,2-c]pyrimidin-1-one.

12. A compound according to claim 3 having the formula:

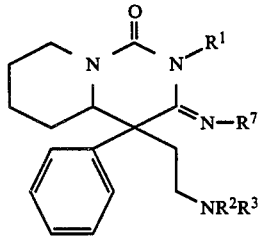

and pharmaceutically acceptable acid addition salts, wherein $R^1$ is —$(CH_2)_n$—Y,
wherein n is 1 or 2;
Y is:
(a) $C_5$–$C_8$ cycloalkyl; or
(b)

(a) $C_5$–$C_8$ cycloalkyl; or

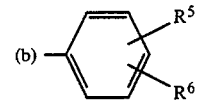

wherein
$R^5$ and $R^6$ independently are:
(a) hydrogen;
(b) $C_1$–$C_6$ alkyl;
(c) $C_1$–$C_6$ alkoxy; or
(d) halogen;
$R^2$ and $R^3$ are independently $C_1$–$C_6$ alkyl; and
$R^7$ is:
(a) hydrogen; or
(b) $C_2$–$C_6$ alkanoyl.

13. A compound according to claim 12, which is (±)trans-4-[2-[bis(1-methylethyl)amino]ethyl]-2-(2-cyclohexylmethyl)octahydro-3-imino-4-phenyl-1H-pyrido[1,2-c]pyrimidin-1-one.

14. A compound according to claim 12, which is (±)trans-4-[2-[bis(1-methylethyl)amino]ethyl]-2-(2-cyclohexylethyl)octahydro-3-imino-4-phenyl-1H-pyrido[1,2-c]pyrimidin-1-one.

15. A compound according to claim 12, which is (±)trans-4-[2-[bis(1-methylethyl)amino]ethyl]octahydro-3-imino-4-phenyl-2-(2-phenylethyl)-1H-pyrido[1,2-c]pyrimidin-1-one.

16. A compound according to claim 12, which is (±)trans-4-[2-[bis(1-methylethyl)amino]ethyl]-2-[2-(3,4-dimethoxyphenyl)ethyl]octahydro-3-imino-4-phenyl-1H-pyrido[1,2c]pyrimidin-1-one.

17. A compound according to claim 12, which is (±)cis-4-[2-[bis(1-methylethyl)amino]ethyl]-2-[2-(3,4-dimethoxyphenyl)ethyl]octahydro-3-imino-4-phenyl-1H-pyrido[1,2-c]pyrimidin-1-one.

18. A compound according to claim 1 having the formula:

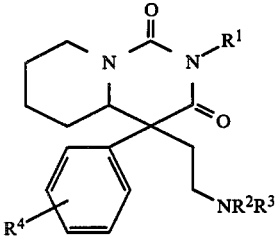

and pharmaceutically acceptable acid addition salts, wherein $R^1$ is:
(a) hydrogen
(b) $C_1$–$C_6$ alkyl;
(c) $C_2$–$C_6$ hydroxyalkyl; or
(d) —$(CH_2)_n$—Y,
wherein
n is 1 or 2;
Y is:
(a) $C_5$–$C_8$ cycloalkyl; or
(b)

(a) $C_5-C_8$ cycloalkyl; or (b) 

wherein
$R^5$ and $R^6$ independently are:
(a) hydrogen;
(b) $C_1-C_6$ alkyl;
(c) $C_1-C_6$ alkoxy; or
(d) halogen;
$R^2$ and $R^3$ are independently $C_1-C_6$ alkyl; and
$R^4$ is:
(a) hydrogen;
(b) $C_1-C_6$ alkyl;
(c) $C_1-C_6$ alkoxy;
(d) halogen; or
(e) phenyl.

19. A compound according to claim 18 wherein $R^4$ is hydrogen.

20. A compound according to claim 19 having the formula:

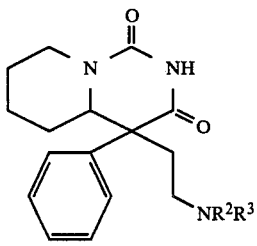

and pharmaceutically acceptable acid addition salts, wherein $R^2$ and $R^3$ are independently $C_1-C_6$ alkyl.

21. A compound according to claim 20, which is (±)trans-4-[2-[bis(1-methylethyl)amino]ethyl]hexahydro-4-phenyl-1H-pyrido[1,2-c]pyrimidine-1,3(2H)-dione.

22. A compound according to claim 19 having the formula:

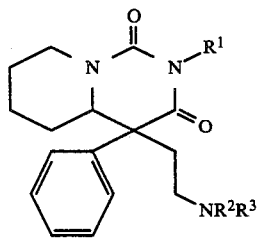

and pharmaceutically acceptable acid addition salts, wherein
$R^1$ is $C_1-C_6$ alkyl; and
$R^2$ and $R^3$ are independently $C_1-C_6$ alkyl.

23. A compound according to claim 22, which is (±)trans-4-[2-[bis(1-methylethyl)amino]ethyl]hexahydro-2-methyl-4-phenyl-1H-pyrido[1,2-c]pyrimidine-1,3(2H)-dione.

24. A pharmaceutical composition comprising at least one compound according to claim 1, together with one or more non-toxic pharmaceutically acceptable carriers.

25. A pharmaceutical composition according to claim 24 wherein said compound is selected from the group consisting of:
(±)trans-3-amino-4-[2-[bis(1-methylethyl)amino)ethyl]-4,4a,5,6,7,8-hexahydro-4-phenyl-1H-pyrido[1,2-c]pyrimidin-1-one,
(±)trans-N-[4-[2-[bis(1-methylethyl)amino]ethyl]-4,4a,5,6,7,8-hexahydro-1-oxo-4-phenyl-1H-pyrido[1,2-c]pyrimidin-3-yl]acetamide,
(±)trans-4-[2-[bis(1-methylethyl)amino]ethyl]octahydro-3-imino-2-methyl-4-phenyl-1H-pyrido[1,2-c]pyrimidin-1-one,
(±)trans-4-[2-[bis(1-methylethyl)amino)ethyl]-2-hexyloctahydro-3-imino-4-phenyl-1H-pyrido[1,2-c]pyrimidin-1-one,
(±)trans-4-[2-[bis(1-methylethyl)amino]ethyl]octahydro-2-(2-hydroxyethyl)-3-imino-4-phenyl-1-H-pyrido[1,2-c]pyrimidin-1-one,
(±)trans-4-[2-[bis(1-methylethyl)amino]ethyl]-2-(2-cyclohexylmethyl)octahydro-3-imino-4-phenyl-1H-pyrido[1,2-c]pyrimidin-1-one,
(±)trans-4-[2-[bis(1-methylethyl)amino]ethyl]-2(2-cyclohexylethyl)octahydro-3-imino-4-phenyl-1H-pyrido[1,2-clpyrimidin-1-one,
(±)trans-4-[2-[bis(1-methylethyl)amino]ethyl]-octahydro-3-imino-4-phenyl-2-(2-phenylethyl)-1H-pyrido[1,2-c]pyrimidin-1-one,
(±)trans-4-[2-[bis(1-methylethyl)amino]ethyl]-2-[2-(3,4-dimethoxyphenyl)ethyl]octahydro-3-imino-4-phenyl-1H-pyrido[1,2-c]pyrimidin-1-one,
(±)cis-4-[2-[bis(1-methylethyl)amino]ethyl]-2-[2-(3,4-dimethoxyphenyl)ethyl]octahydro-3-imino-4-phenyl-1H-pyrido[1,2-c]pyrimidin-1-one,
(±)trans-4-[2-[bis(1-methylethyl)amino)ethyl]hexahydro-4-phenyl-1H-pyrido[1,2-c]pyrimidine-1,3(2H)-dione, and
(±)trans-4-[2-[bis(1-methylethyl)amino)ethyl]hexahydro-2-methyl-4-phenyl-1H-pyrido[1,2-c]pyrimidine-1,3(2H)-dione.

26. A method for treating cardiac arrhythmia in mammals comprising administering a therapeutically effective amount of at least one compound of claim 1 to a mammal in need of such treatment.

27. A method according to claim 26 wherein said compound is selected from the group consisting of:
(±)trans-3-amino-4-[2-[bis(1-methylethyl)amino]ethyl]-4,4a,5,6,7,8-hexahydro-4-phenyl-1H-pyrido[1,2-c]pyrimidin-1-one,
(±)trans-N-[4-[2-[bis(1-methylethyl)amino]ethyl]-4,4a,5,6,7,8-hexahydro-1-oxo-4-phenyl-1H-pyrido[1,2-c]pyrimidin-3-yl]acetamide,
(±)trans-4-[2-[bis(1-methylethyl)amino]ethyl]octahydro-3-imino-2-methyl-4-phenyl-1H-pyrido[1,2-c]pyrimidin-1-one,
(±)trans-4-[2-[bis(1-methylethyl)amino]ethyl]-2-hexyloctahydro-3-imino-4-phenyl-1H-pyrido[1,2-c]pyrimidin-1-one,
(±)trans-4-[2-[bis(1-methylethyl)amino]ethyl]octahydro-2-(2-hydroxyethyl)-3-imino-4-phenyl-1H-pyrido[1,2-c]pyrimidin-1-one,
(±)trans-4-[2-[bis(1-methylethyl)amino]ethyl]-2(2-cyclohexylmethyl)octahydro-3-imino-4-phenyl-1H-pyrido[1,2-c]pyrimidin-1-one,
(±)trans-4-[2-[bis(1-methylethyl)amino]ethyl]-2-(2-cyclohexylethyl)octahydro-3-imino-4-phenyl-1H-pyrido[1,2-c]pyrimidin-1-one, (±)trans-4-[2-[bis(1-methylethyl)amino]ethyl]-octahydro-3-imino-4-phenyl-2-(2-phenylethyl)-1H-pyrido[1,2-c]pyrimidin-1-one, (±)trans-4-[2-[bis(1-methylethyl)amino]ethyl]-2-[2-(3,4-dimethoxyphenyl)ethyl]octahydro-3-imino-4-phenyl-1H-pyrido[1,2-c]pyrimidin-1-one, (±)cis-4-[2-[bis(1-methylethyl)amino]ethyl]-2-[2-(3,4-dimethoxyphenyl)ethyl]octahydro-3-imino-4-phenyl-1H-pyrido[1,2-c]pyrimidin-1-one, (±)trans-4-[2-[bis(1-methylethyl)amino]ethyl]hexahydro-4-phenyl-1H-pyrido[1,2-c]pyrimidine-1,3(2H)-dione, and (±)trans-4-[2-[bis(1-methylethyl)amino]ethyl]hexahydro-2-methyl-4-phenyl-1H-pyrido[1,2-c]pyrimidine-1,3(2H)-dione.

* * * * *